United States Patent [19]

Reid et al.

[11] 4,373,813

[45] Feb. 15, 1983

[54] CONTROL OF SYSTEM ENERGY IN A SINGLE BEAM SPECTROPHOTOMETER

[75] Inventors: Taylor A. Reid, Newport Beach; James A. Miller, Fullerton; Duane G. Barber, Yorba Linda, all of Calif.

[73] Assignee: Beckman Instruments, Inc., Fullerton, Calif.

[21] Appl. No.: 223,054

[22] Filed: Jan. 7, 1981

[51] Int. Cl.³ .............................................. G01J 3/42
[52] U.S. Cl. .................................................. 356/326
[58] Field of Search ................ 356/319, 320, 323–326, 356/328; 364/498

[56] References Cited

U.S. PATENT DOCUMENTS 3,680,957 8/1972 Fukuda ............................... 356/325

FOREIGN PATENT DOCUMENTS 54-159283 12/1979 Japan .................................... 356/319
55-126834 10/1980 Japan .................................... 356/319

OTHER PUBLICATIONS

Jupijn et al., *J. Phys. E: Sci. Instrum.*, vol. 12, No. 4, Apr. 1979, pp. 294–297.

*Primary Examiner*—F. L. Evans
*Attorney, Agent, or Firm*—R. J. Steinmeyer; Robert R. Meads; John R. Shewmaker

[57] ABSTRACT

A single beam spectrophotometer is conditioned to automatically scan a sample across a wavelength scan range and to measure the sample at selected wavelengths within the range. Methods of setting output signal gain, adjusting signal gain for a selected wavelength range, and automatically scanning and measuring the sample are disclosed.

1 Claim, 3 Drawing Figures

H.V. DYNODE HIGH VOLTAGE vs. GAIN TABLE

| BITS | GAIN | H.V. |
|------|------|------|
| 50 | 1 | 177.5 |
| 55 | 1.5 | 195 |
| 60 | 2.3 | 213 |
| 65 | 3.3 | 230 |
| 70 | 5.0 | 248 |
| 75 | 7.0 | 266 |
| 80 | 9.8 | 284 |
| 85 | 13.1 | 301 |
| 90 | 17.3 | 319 |
| 95 | 23 | 337 |
| 100 | 31 | 355 |
| 105 | 39 | 372 |
| 110 | 48 | 390 |
| 115 | 59 | 408 |
| 120 | 75 | 426 |
| 125 | 91 | 443 |
| 130 | 109 | 461 |
| 135 | 128 | 479 |
| 140 | 154 | 497 |
| 145 | 182 | 514 |
| 150 | 214 | 532 |
| 155 | 254 | 550 |
| 160 | 295 | 568 |
| 165 | 345 | 585 |
| 170 | 409 | 603 |
| 175 | 468 | 621 |
| 180 | 554 | 639 |
| 185 | 627 | 656 |
| 190 | 704 | 674 |
| 195 | 818 | 692 |
| 200 | 909 | 710 |

FIG. 3

CONTROL OF SYSTEM ENERGY IN A SINGLE BEAM SPECTROPHOTOMETER

BACKGROUND OF THE INVENTION

1. Field of the Invention

The present invention relates to single beam spectrophotometers and, more particularly, to the measurement of a sample in a single-beam spectrophotometer at one or more different light wavelength settings.

2. Description of the Prior Art

In a spectrophotometer a sample to be measured is positioned in a light beam and light transmitted, scattered, or otherwise passed or radiated by the sample is directed to a light detector, such as a multiplier phototube, which generates an output current signal proportional to the intensity of the detected light. It is often desired to measure the sample at different light wavelengths and, for that purpose, a wavelength dispersing mechanism, such as a monochromator, is positioned in the light path to select and control the wavelengths of light reaching the detector. The monochromator is adjustable to and through numerous individual wavelength settings across the light spectrum. At each setting the monochromator passes light at only a corresponding selected wavelength(s).

Sample measurements at different wavelength settings are complicated by the fact that a spectrophotometer's system energy varies as a function of wavelength. In other words, the detector output signal for 100% transmittance is different at one wavelength than the corresponding 100% transmittance output signal at another wavelength. So called double-beam spectrophotometers solve the wavelength dependent system energy problem by splitting the light beam into sample and reference beams, by sensing the energy change in the reference beam as the monochromator scans different wavelength settings, and by constantly adjusting dynode voltage of the photomultiplier detector to maintain a constant detector output signal for the reference beam changes. In this manner the output signal is maintained at a constant corrected level as the various wavelength settings are scanned. Unfortunately, such constant, repetitive dynode voltage correction introduces undesired output signal noise because of the many small corrections of detector voltage. In addition, by splitting the light beam, a double-beam system inherently reduces the energy remaining for the sample beam thereby magnifying the effect of the output signal noise.

Single beam instruments, on the other hand, are limited in ability to measure a sample across a wavelength scan range due to the fact that only a single dynode voltage is employed for the photomultiplier detector. To reduce detector output signal noise, the dynode voltage level is chosen to give a maximum or optimum output signal level. But since the detector inherently exhibits a limited dynamic range, the optimum dynode voltage, though optimum at one or some wavelengths, may cause the detector to saturate at other wavelengths. Moreover, single beam spectrophotometers require operator intervention to calibrate or set system gain at an optimum value prior for each wavelength setting at which a sample is to be measured and prior to the sample measurement at each setting. Moreover, a single beam system, by its single beam nature alone, measures a sample and a reference at different times in the same single beam, and operator intervention is required to make the two required measurements at each wavelength setting.

SUMMARY OF THE INVENTION

The present invention resides in a novel method of controlling a single-beam spectrophotometer in a manner enabling the spectrophotometer to measure a sample in a selected wavelength range without the drawbacks of the prior art. The method is simple in operation and straightforward in implementation and is particularly adapted to control system energy in a single-beam spectrophotometer in a manner enabling sample measurements to be made at wavelength settings of the selected wavelength range without further energy adjustment at each setting.

Generally speaking, the method of the invention in its broadest aspect contemplates the steps of (1) developing a light energy vs. wavelength profile for the spectrophotometer by measuring the output signal at a plurality of different wavelength settings, (2) storing the measured values of output signal vs. wavelength, (3) selecting a range of wavelength settings for measuring a sample, (4) and setting the spectrophotometer at a first wavelength setting of the selected range. The method further includes (5) adjusting output signal gain of the spectrophotometer at the first wavelength setting until the output signal achieves a maximum or optimum value. Thereafter, (6) a ratio is developed from the stored output signal vs. wavelength profile of the value of the stored output signal at the first wavelength setting in relation to the maximum of the stored output signal within the range of wavelengths selected in step (3). Having developed the ratio, (7) the spectrophotometer output signal gain is adjusted at the first wavelength setting until the output signal bears the same ratio to the maximum value of the output signal developed in step (5) as the ratio developed in step (6). Such adjustment of the output signal gain reduces system energy to a value for the first wavelength setting in the selected range enabling other wavelength settings in the range to thereafter be scanned and measured without saturating the photomultiplier detector.

BRIEF DESCRIPTION OF THE DRAWINGS

FIG. 3 is a profile of photomultiplier gain v. dynode voltage.

DESCRIPTION OF THE PREFERRED EMBODIMENT

Figure 1:
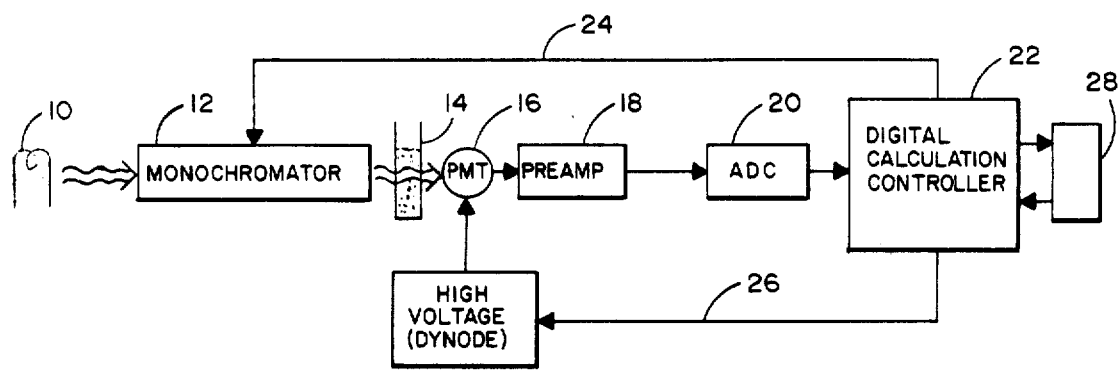
FIG. 1 is a block diagram of a single-beam spectrophotometer implementing the method of the present invention.

For purposes of illustration, the method of the present invention will be described with reference to the single-beam spectrophotometer system illustrated in FIG. 1. The single-beam spectrophotometer including a light source 10, light energy from which is directed to a monochromator 12. Light exiting the monochromator is directed through a sample compartment 14 to a photomultiplier detector 16. Light source 10 may be a tungsten halogen lamp. Monochromator 12 is controllable in a conventional manner to restrict or limit the wavelengths of light and passes only a selected and variable narrow bandwidth of light toward sample compartment 14 and detector 16. Photomultiplier detector 16 provides a measure of the transmittance or absorbance of the sample by detecting the amount of light energy passed by or otherwise radiating from the sample and generates an output current signal providing a measure thereof. The detector output signal is amplified at 18 and converted to digital form by A-D converter 20. The digital signal is then supplied to a data acquisition and control system 22.

System 22 is either a hard-wired controller or a programmable microcomputer well known in the art. Control signals are supplied by the control system over respective control lines 24 and 26 to control the wavelength setting of monochromator 12 and the dynode voltage setting of detector 16, respectively. It is understood that the particular hardware arrangement of such a microcomputer is well known in the art and forms no part of the present invention. In general, however, such general purpose computers include a central processing unit, a program sequence of memory instructions (a read-only memory), an uncommitted block of usable memory (a read/write memory), and various input and output interfacing capabilities. Instructions can be executed from the read-only memory. Data can be transferred into or out of the read/write memory and into or out of the central processing unit. The central processing unit is configured to fetch and/or execute data and/or instructions to and/or from the memories and to the various input and output control devices. Programming such a computer for automated method implementation and operation and coordinating information processing is straightforward and well established in the art.

Figure 2:
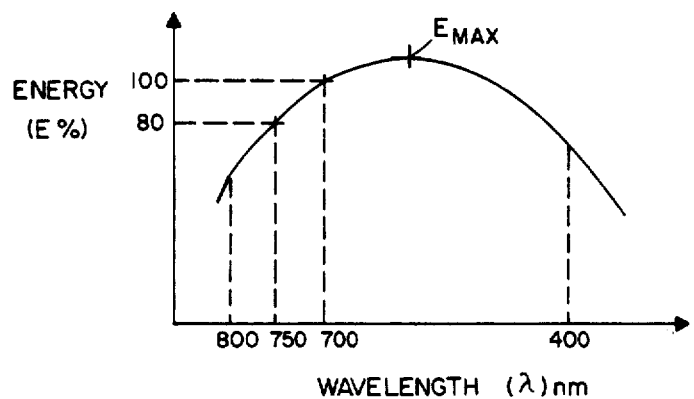
FIG. 2 is a system energy profile for the spectrophotometer as a function of wavelength.

Referring now to FIG. 2, a system energy profile is depicted for the overall FIG. 1 spectrophotometer including source, monochromator, detector, mirrors, filters and all other operating elements. The profile illustrates the system energy at 100% transmittance as a function of wavelength. For the FIG. 1 system the wavelength range is illustrated between about 800 and 400 nanometers and it is seen that as the wavelength setting is lowered from 800 nanometers the 100% transmittance system energy increases to a maximum and then decreases as the 400 nanometer setting is approached.

In accordance with one aspect of the invention a light energy vs. wavelength profile for the spectrophotometer similar to FIG. 2 is developed by measuring the output of detector 16 at a plurality of different wavelength settings of monochromator 12 and by storing the measured values in a storage segment 28 of controller 22. The storage segment 28 may take any convenient form of read-only memory. If the invention is practiced on a manual instrument, without a control system 22, the spectral information can be stored as positions or conditions of impedance network or as potentiometer settings.

With the light energy vs. wavelength profile for the spectrophotometer stored by system 22, a range of wavelength settings at and across which a sample scanning operation is to be performed is selected. Typically such range will be a limited portion of the overall range of wavelengths measurable by the system.

Having selected a range of wavelengths to be scanned, the photomultiplier gain is adjusted in the absence of a sample (or with a sample blank in sample compartment 14) to provide a signal large enough for accurate measurement by the system components but small enough to be within the signal handling range of the system components. Such gain adjustment establishes an optimum gain setting for the spectrophotometer at a selected wavelength within the range of wavelengths to be scanned. In the absence of a sample the optimum gain setting establishes the maximum output signal level at 100% sample transmittance. To this end controller 22 issues a digital control signal over line 24 for setting monochromator 12 at a first wavelength setting of the selected range of wavelength settings to be scanned. Controller 22 then issues one or more successive digital control signals over control line 26 adjusting dynode voltage of detector 16 until the output signal achieves the desired optimum or maximum value.

For implementing the foregoing gain setting procedure, in accordance with another aspect of the invention, a gain v. dynode voltage profile for the photomultiplier similar to FIG. 3 is developed and stored in storage segment 28 of the controller 22. At the selected wavelength setting a first dynode voltage level is set to establish the output signal at some value—typically a minimum value. The value of the output signal is then measured and compared to the desired optimum or maximum value therefor. Significantly controller 22 employs the stored gain v. dynode voltage profile to calculate and set a new dynode voltage level for establishing the output signal at the desired value. The foregoing steps are automatically repeated for each dynode voltage setting until the desired optimum or maximum output signal is attained within a desired tolerance. The controller then stores the output signal value at the selected wavelength for later use. Such storage of the gain v. dynode voltage profile allows rapid gain setting without operator intervention thereby conditioning the spectrophotometer for rapid sample measurements.

In accordance with a further aspect of the invention, controller 22 develops from the energy vs. energy wavelength profile stored therein a ratio of (a) the value of the stored output signal at the first selected wavelength setting in relation to (b) the maximum of the stored output signal within the range of wavelengths selected to be scanned. In other words, this ratio defines the maximum proportional change in the output signal level which would result when the scanning operation is executed across the range of wavelengths exhibiting the variable system energy profile illustrated in FIG. 2.

Since the output signal level was set at a maximum at the first selected wavelength setting of the selected range, the invention further comprises the step of adjusting spectrophotometer output signal gain at the first wavelength setting until the output signal bears the same ratio to the maximum value of the output signal as the ratio just calculated. This reduction in gain is executed by controller 22 issuing a digital control signal over line 26 reducing the photomultiplier dynode voltage an appropriate amount. As a result of this last adjustment, the output signal level at the first wavelength setting of the selected range is reduced to a level allowing the full selected range to be scanned without exceeding the maximum output signal level of the system.

Referring to FIG. 2, a representative range of wavelengths to be scanned is illustrated between 750 and 7000 nanometers. Corresponding light energy values of 100% T are 80 and 100 as shown. Assume the first wavelength setting is set at 750 nanometers, and the output signal level is set at the maximum value thereof. It is seen that scanning could not be accomplished since moving from 750 to 700 nanometers would saturate the photomultiplier. Accordingly, the aforedescribed method reduces the output signal at the first wavelength setting (e.g. 750 nanometers) by the ratio 80/100=0.8. By reducing the output signal level to 0.8 of its maximum value, the system will then accommodate an increase in the output signal level thereafter toward its maximum value as the monochromator 12 scans toward 700 nanometers.

After adjusting the spectrophotometer gain as aforedescribed, the scanning operation now proceeds. To this end in accordance with a further aspect of the invention, two scans are executed, a first background scan with a blank sample or no sample in sample compartment 14 and a second scan with an actual sample in place. During the scanning operation measurements may be taken at as many wavelength settings as desired, for example, 280 points in the preferred embodiment. The readings derived for the background scan are stored in a corresponding storage segment of processor 22. Thereafter, a sample is positioned in the sample compartment and the same wavelength range is again scanned to derive sample measurements. If making transmittance measurements, the processor 22 automatically calculates the ratio at each wavelength setting of the stored background reading with the measured sample reading. If the ratio is one, such corresponds to a 100% transmittance reading. If the ratio is less than one, it indicates sample absorption of a certain amount. Such percent transmittance ratioing in effect digitally corrects for the energy change occurring as a function of wavelength. When measurements are made in absorbance units, subtraction of background readings from sample readings provides equivalent results. Such storage of the background system energy values enables sample measurements to be executed in sequence at the wavelength settings without operator intervention and without interruption for background measurement at each setting thereby enabling a scanning operation to be automatically and rapidly completed.

By virtue of the foregoing method, the maximum system energy of a single-beam spectrophotometer is controlled in a manner allowing the spectrophotometer to execute a scanning operation for measuring the sample at plural wavelength settings without exceeding its maximum energy and without changing or adjusting the photomultiplier dynode voltage or other gain change elements during the course of the actual scan.

While preferred embodiments of the invention have been illustrated and described, various modifications may be made therein without departing from the invention as set forth in the appended claims. What is claimed is:

1. For use in a single-beam spectrophotometer which comprises a light source for illuminating a sample with light energy, a detector for receiving light energy from the sample and generating an output signal proportional thereto, means for changing the wavelength setting of light energy received by the detector, and means for changing output signal gain of the spectrophotometer, a method of controlling maximum system energy during measurement of a sample at a plurality of different wavelength settings within a range of wavelength settings for which system energy varies with wavelength comprising the steps of:

(1) developing a light energy vs. wavelength profile for the spectrophotometer by measuring the output signal at a plurality of different wavelength settings;

(2) storing the measured values of output signal vs. wavelength developed in step (1);

(3) selecting a range of wavelength settings for measuring a sample;

(4) setting the spectrophotometer at a first wavelength setting in the selected range;

(5) adjusting output signal gain of the spectrophotometer at the first wavelength setting until the output signal achieves a maximum or optimum value;

(6) developing from the stored output signal vs. wavelength profile a ratio of (a) the value of the stored output signal at the first wavelength setting in relation to (b) the maximum value of the stored output signal within the range of wavelength settings selected in step (3); and (7) adjusting spectrophotometer output signal gain at the first wavelength setting until the output signal bears the same ratio to the maximum value of the output signal in step (5) as the ratio developed in step (6), whereby sample measurement at wavelength settings within the selected wavelength range may thereafter be executed without saturating the detector.

* * * * *